United States Patent
Seavey (10) Patent No.: US 9,687,320 B2
(45) Date of Patent: Jun. 27, 2017

(54) DENTAL DEVICE FOR ANCHORING A DENTURE TO AN IMPLANT

(71) Applicant: Sterngold Dental, LLC, Attleboro, MA (US)

(72) Inventor: Bruce Seavey, North Attleboro, MA (US)

(73) Assignee: Sterngold Dental, LLC, Attleboro, MA (US)

(*) Notice: Subject to any disclaimer, the term of this patent is extended or adjusted under 35 U.S.C. 154(b) by 235 days.

(21) Appl. No.: 14/181,891

(22) Filed: Feb. 17, 2014

(65) Prior Publication Data

US 2015/0230892 A1     Aug. 20, 2015

(51) Int. Cl.
*A61C 8/00*     (2006.01)
(52) U.S. Cl.
CPC .......... *A61C 8/0053* (2013.01); *A61C 8/0022* (2013.01); *A61C 8/0054* (2013.01); *A61C 8/0068* (2013.01)
(58) Field of Classification Search
CPC .................................................. A61C 8/0053
See application file for complete search history.

(56) References Cited

U.S. PATENT DOCUMENTS

| | | | |
|---|---|---|---|
| 3,732,621 A | 5/1973 | Bostrom | |
| 4,832,601 A * | 5/1989 | Linden | A61C 8/005 433/173 |
| 4,907,969 A * | 3/1990 | Ward | A61C 8/005 433/173 |
| 5,073,110 A * | 12/1991 | Barbone | A61C 8/0001 433/173 |
| 5,564,922 A * | 10/1996 | Rosa | A61C 8/005 433/173 |
| 5,564,925 A | 10/1996 | Shampanier | |
| 6,299,447 B1 * | 10/2001 | Zuest | A61C 8/0048 433/172 |

(Continued)

FOREIGN PATENT DOCUMENTS

| | | |
|---|---|---|
| DE | 20 2004 016896 U1 | 3/2005 |
| DE | 20 2006 012016 U1 | 11/2006 |

(Continued)

OTHER PUBLICATIONS

Extended European Search Report of Application No. 15155352.6-1658, mailed Apr. 5, 2015.

*Primary Examiner* — Ralph Lewis
(74) *Attorney, Agent, or Firm* — Wiggin and Dana LLP; Gregory S. Rosenblatt; Jonathan D. Hall (57) ABSTRACT

A dental device for anchoring a dental appliance within a patient's mouth, including an abutment with a distal end characterized by a substantially concave surface and a first hollow, a pivotable collar with a substantially convex bottom and a second hallow formed through it from top to bottom, and an attachment screw. The bottom of the pivotable collar is configured to pivotally rest against the concave surface of the abutment. The attachment screw is configured to extend partially through the collar and connect with the abutment so as to secure the collar to the abutment. When not secured, the collar can be angulated relative to the abutment to provide for the orientation of a dental prosthesis within a patient's mouth.

9 Claims, 7 Drawing Sheets

(56) References Cited

U.S. PATENT DOCUMENTS

| | | | | |
|---|---|---|---|---|
| 6,500,003 | B2* | 12/2002 | Nichinonni | A61C 8/005 433/173 |
| 6,843,653 | B2* | 1/2005 | Carlton | A61C 8/005 433/174 |
| 7,214,063 | B2* | 5/2007 | Cohen | A61C 8/005 433/173 |
| 8,684,733 | B2* | 4/2014 | McBride | A61C 8/0053 433/173 |

FOREIGN PATENT DOCUMENTS

| | | |
|---|---|---|
| DE | 10 2011 081208 A1 | 2/2013 |
| WO | 92/03984 A1 | 3/1992 |

\* cited by examiner

DENTAL DEVICE FOR ANCHORING A DENTURE TO AN IMPLANT

FIELD OF THE DISCLOSURE

The subject matter of the present disclosure generally relates to dental devices, and more particularly relates to a device for aiding in the angled securement of a dental appliance within a patient's mouth.

BACKGROUND OF THE DISCLOSURE

Many individuals experience tooth loss, due to age, trauma, or other affliction. Such loss can impair certain abilities, such as the ability to chew food. Moreover, many individuals view a missing tooth or teeth as cosmetically undesirable. These circumstances have long given rise to artificial teeth and other dental appliances, the nature and operational manner of which vary widely.

Dental appliances can present numerous obstacles. For artificial teeth, a suitable anchoring must be made within the mouth of the patient to provide sufficient durability for intended use. This often requires drilling into, or otherwise attaching an anchor to, the bone of the patient's mouth. In such devices, both the attachment and the dental appliance itself must be capable of prolonged exposures to the rigors of the mouth, such as moisture and the forces associated with chewing, without degradation at an unsatisfactory rate.

Due to irregularities in the mouths of individual patients, such as bone structure and positioning of remaining teeth, it is often necessary that artificial teeth be disposed at particular orientations. There exist various devices that seek to overcome this obstacle, including one-piece attachment mechanisms, ball shaped attachments and other devices, many of which screw directly into an implant to retain a denture. For example, U.S. Pat. Nos. 6,843,653, 6,146,383 and 3,732,621, the respective disclosures of which are all incorporated by reference herein in their entirety, all disclose such dental devices. However, such abutments do not perform well when the corresponding implants are angled beyond a few degrees. In particular, one-piece ball shaped abutments have been used to connect overdentures to implants. However, when these implants are not approximately parallel to each other, the corresponding denture cannot be easily seated. Such a condition results in excessive wear, thereby resulting in malfunction, user discomfort and the attendant negatives of corresponding replacement or repair efforts.

The subject matter of the present disclosure is directed to overcoming, or at least reducing the effects of, one or more of the problems set forth above.

BRIEF SUMMARY OF THE DISCLOSURE

Disclosed is a dental device useful in securement of various dental appliances within a patient's mouth. Generally, a pivotable collar having a hemispherical convex bottom and a hollow formed through it is capable of selective and fixable angular orientation.

Described herein are various embodiments in which the pivotable collar is utilized with additional hardware. For instance, in a particular embodiment, a dental implant is affixed to a patient's jawbone and a cylindrical abutment is affixed to the dental implant. The top of the abutment protrudes above the patient's soft issue. The top of the abutment has a hemispherical concave surface and contains an internal hole, which is preferably threaded. The pivotable collar is placed on top of the abutment and an attachment screw passes through the collar, connecting it to the abutment. A top cap is connected to the collar and secured into a denture. The collar may be pivoted in many angles prior to its securement to compensate for the angulation of the implant. Damage and wear of the parts is limited, thereby overcoming at least one of the deficiencies of previous designs.

BRIEF DESCRIPTION OF THE DRAWINGS

The foregoing summary, preferred embodiments, and other aspects of the present disclosure will be best understood with reference to a detailed description of specific embodiments, which follows, when read in conjunction with the accompanying drawings, in which.

Like reference numbers and designations in the various drawings indicate like elements.

DETAILED DESCRIPTION

Disclosed is a dental device for aiding in the anchoring a dental appliance to a patient's mouth.

Figure 1A:
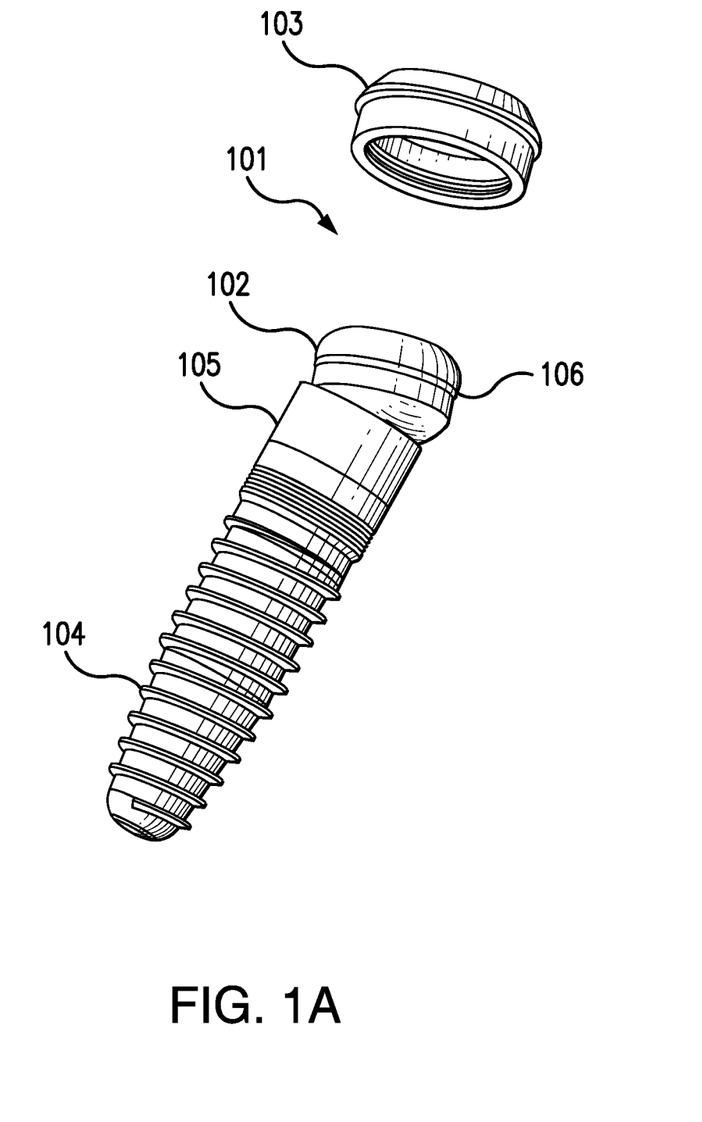
FIG. 1A is a blow-up illustration of an embodiment having a pivotable collar and a top cap.

FIG. 1A is a blow-up side view of an embodiment dental device 101 with certain accompanying hardware. Dental device 101 includes pivotable collar 102 and top cap 103. It is noted that Anchor 104 and abutment 105 may be any suitable anchor or abutment, many of which will be apparent to those of skill in the art to which the present disclosure relates. Further discussion the features of such anchors and abutments is limited so as to not to obscure the new subject matter of the present disclosure. Top cap 103 is configured to connect to pivotable collar 102. Preferably, top cap 103 is generally cylindrical in shape, with a height less than its diameter, and has disposed in it an opening for attachment onto pivotable collar 102. The outer surface of top cap 103 may optionally have disposed on its side exterior structure to facilitate its connection to a dental prosthesis. In the embodiment, top cap 103 is seated onto pivotable collar 102. To this end, disposed on the outer surface of collar 102 is optional horizontal circumferential detent 106, which is configured to facilitate the connection of top cap 103 onto pivotable collar 102. It should be noted that various other structure may be suitable for interconnection of pivotable collar 102 and top cap 103.

Figure 1B:
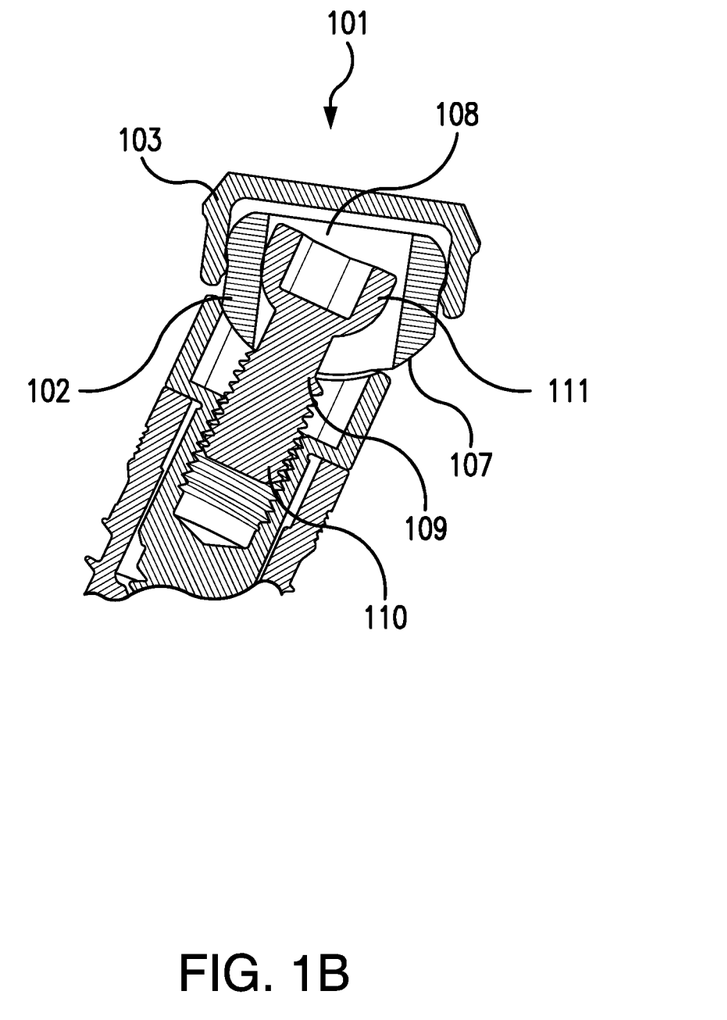
FIG. 1B is schematic cut-away side view of the embodiment of FIG. 1A.

Now in reference to FIG. 1B, which is a cut-away side view of dental device 101, pivotable collar 102 has convex bottom 107 which is substantially hemispherical. Pivotable collar 102 also has formed through it hollow 108, which extends from top to bottom. The embodiment also includes retention device 109, with which pivotable collar 102 is configured to fixably engage. When retention device 109 and pivotable collar 102 are not fixably engaged, the orientation of pivotable collar 102 is adjustable, allowing angulation of pivotable collar 102 and top cap 103 in respect to anchor 104 and abutment 105. Such angulation facilitates the correct orientation of a dental prosthetic connected to top cap 103 within a patient's mouth. In certain constructed embodiments, angulation of approximately 18 degrees was obtained, thus helping to address the deficiencies of previously existing designs. The fixable engagement of pivotable collar 102 and retention device 109 prevents reorientation of pivotable collar 102, allowing selection of a particular desired angle for a dental prosthetic attached to dental device 101.

Preferably, hollow 108 is substantially cylindrical in shape, and retention device 109 is an attachment screw having threaded end 110 and distal end 111. In the embodiment, distal end 111 has a greater circumference than threated end 110, allowing distal end 111 to fixably engage with hollow 108 of pivotable collar 102. Optionally, convex bottom 107 is textured in a manner effective to facilitate the engagement of pivotable collar 102 and retention device 109. It should be understood that various alternate retention devices are suitable for use with pivotable collar 102 and top cap 103, which may operate, for instance, by snapping into place.

Figure 1C:
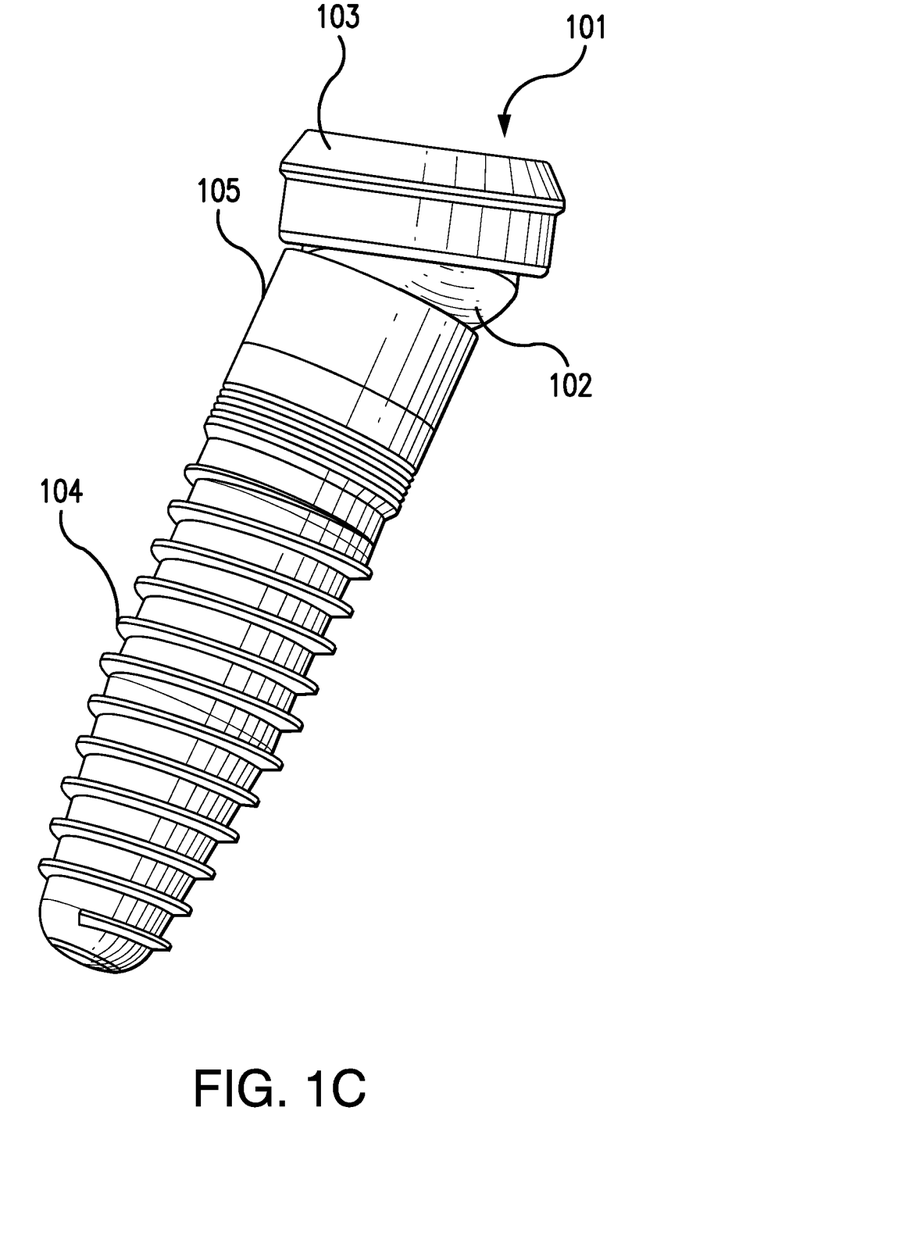
FIG. 1C is an illustration of the assembled device of the embodiment of FIG. 1A, complete with an anchor and an abutment.

FIG. 1C is an illustrative depiction of dental device 101 where top cap 103 is connected to pivotable collar 102, with pivotable collar 102 secured to abutment 105 by retention device 109 (not shown). Dental device 101 is angulated in reference to anchor 104 and abutment 105.

Generally, materials suited for use with the present disclosure will be resistant to degradation within a patient's mouth and non-toxic to humans. Pivotable collar 102 and top cap 103 may be constructed from various materials that will be apparent to those of skill in the art to which the present disclosure pertains. Particularly, pivotable collar 102 may be optionally formed from substantially pure titanium, a titanium alloy coated with titanium nitride or optionally from stainless steel. Top cap 103 may be optionally formed from nylon, polyurethane, or rubber.

Figure 2A:
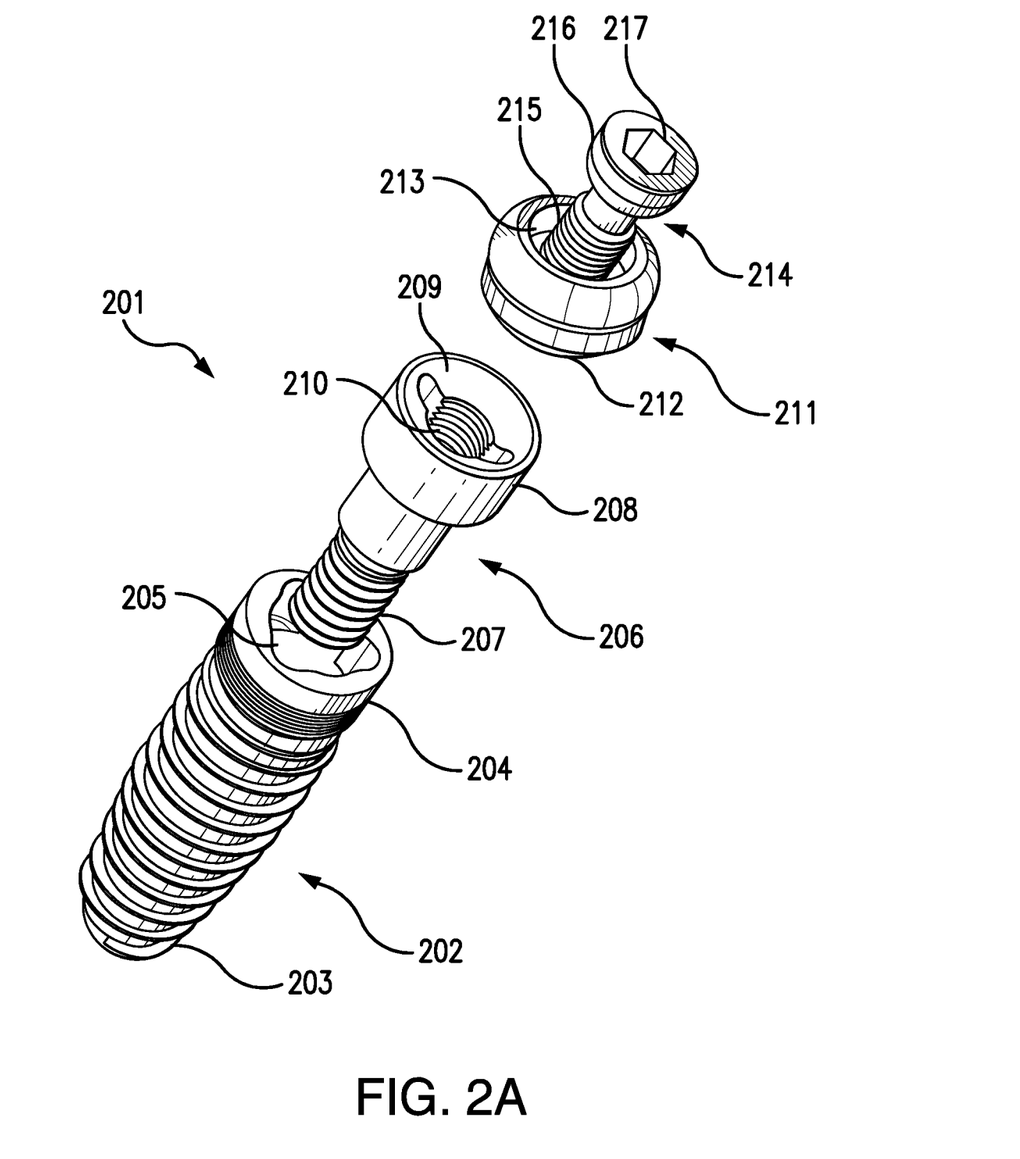
FIG. 2A is a blow-up illustration of an embodiment having an anchor and an abutment.

FIG. 2A is a blown-up illustration depicting dental device 201, which includes several components. Anchor 202 has insertion end 203 and distal end 204. Distal end 204 has formed therein first hollow 205. Abutment 206 has insertion end 207 and distal end 208. Distal end 208 of abutment 206 has hemispherical concave surface 209 and has formed in it second hollow 210. Insertion end 207 of abutment 206 is connectable within first hollow 205 of anchor 202. Pivotable collar 211 has hemispherical convex bottom 212. Preferably, pivotable collar 211 is substantially ball shaped in its general form. Pivotable collar 211 also has formed in it third hallow 213. Bottom 212 of pivotable collar 211 is configured to pivotally rest against concave surface 209 of abutment 206. Attachment screw 214 has insertion end 215 and distal end 216. Attachment screw 214 is configured to extend partially through pivotable collar 211 so that insertion end 215 is interconnected with second hollow 210 so as to secure pivotable collar 211 to abutment 206. In the embodiment, distal end 216 of attachment screw 214 has a circumference that is larger than that of insertion end 215, thereby providing a mechanism for securement of pivotable collar 211. Optionally, attachment screw 214 has formed thereon detent 217 for turning attachment screw 214 so as to interconnect it with abutment 206.

Figure 2B:
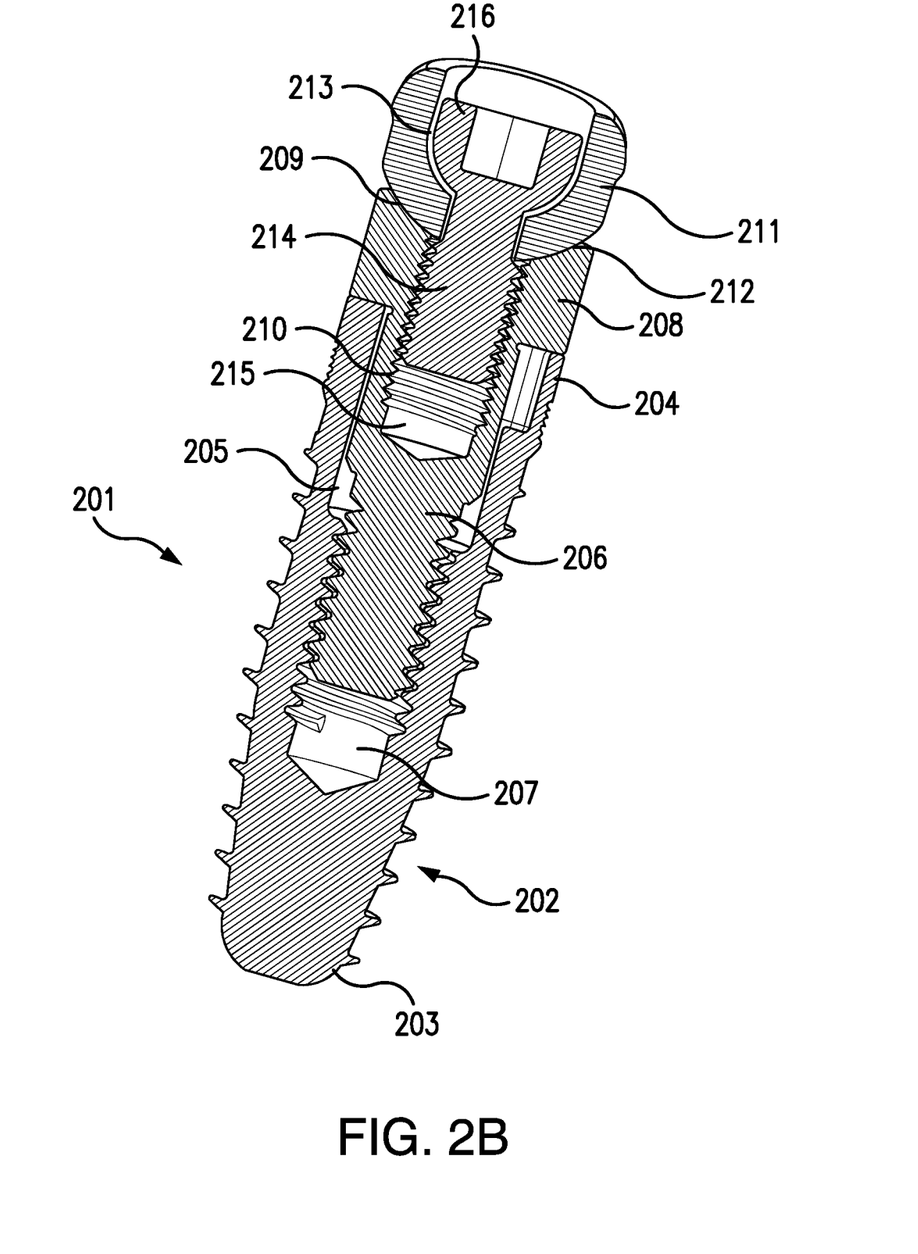
FIG. 2B is a schematic cut-away side view of the embodiment of FIG. 2A.

FIG. 2B is a schematic cut-away side view of the embodiment of FIG. 2B. In the embodiment, distal end 216 of attachment screw 214 is substantially disposed within third hollow 213 of collar 211 when insertion end 215 of attachment screw 214 is interconnected with second hollow 210 of abutment 206. In such an optional configuration, attachment screw 214 does not protrude above the top of dental device 201.

Pivotable collar 211 may be pivotally adjusted in any appropriate direction and then locked in place using attachment screw 214. Once pivotable collar 211 is locked in place, a top cap (not pictured) is placed over the device. The top cap is then processed into the denture, thereby providing retention and stability for the denture. The use of top caps allows appropriate retention of a denture and provides for longer use than certain other designs.

It should be understood that a single unit of the disclosed device may be used to attach an artificial tooth. A number of the disclosed devices may be used in conjunction to attach a set of artificial teeth or a denture.

Figure 3:
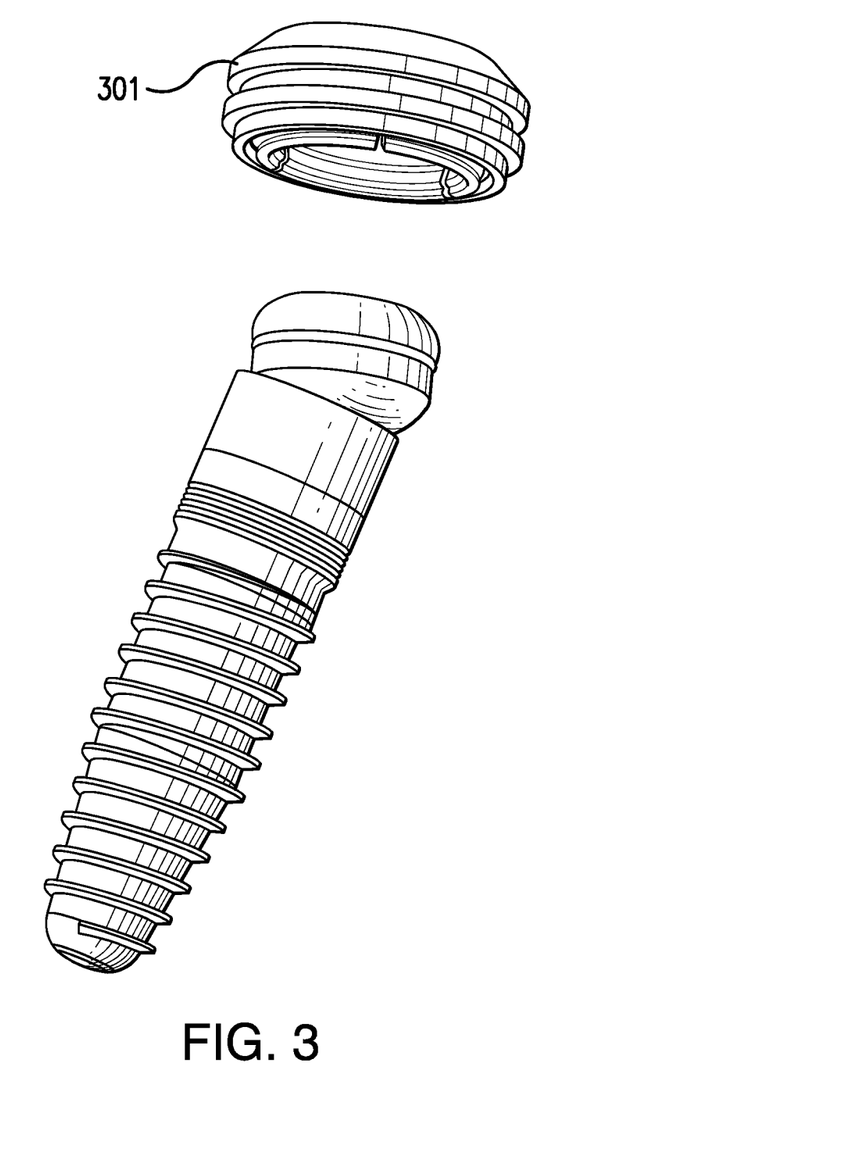
FIG. 3 is a blow-up illustration of an embodiment in which the top cap is encapsulated in a metallic housing.

FIG. 3 depicts an embodiment in which metallic enclosure 301 is placed over top cap (not shown). Such a configuration provides certain advantages that will be recognizable to those of skill in the art to which the present disclosure pertains.

Figure 4:
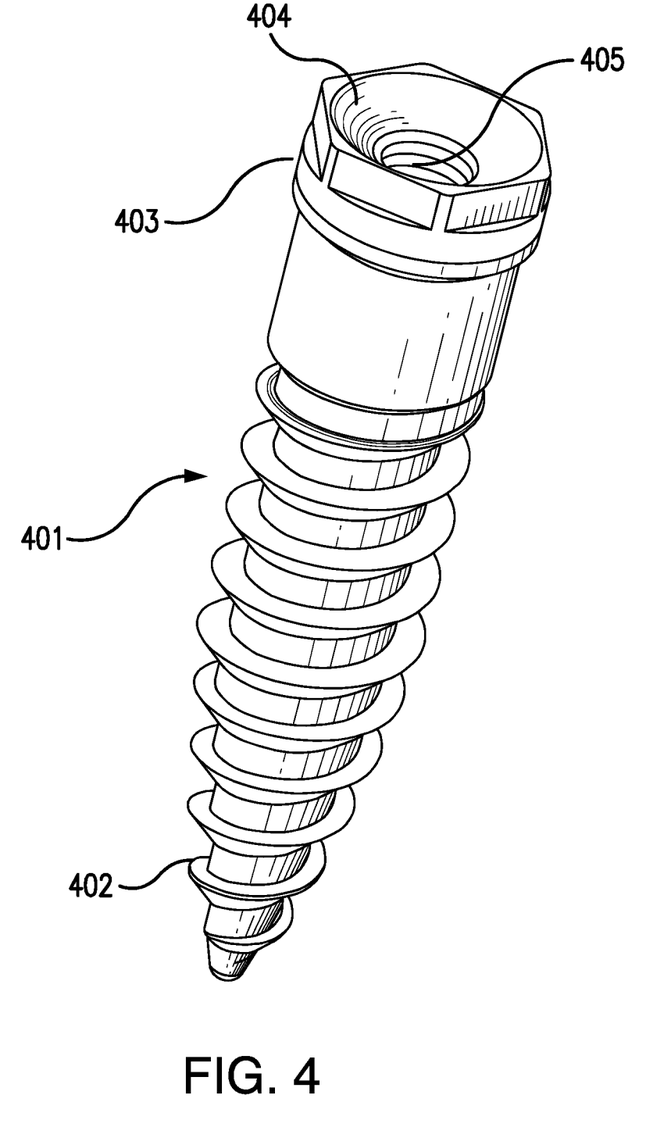
FIG. 4 is a illustration of a one piece anchor abutment having a hemispherical concave surface for interfacing with a pivotable collar.

FIG. 4 depicts single piece anchor abutment 401, useful in combination with the disclosed embodiment dental devices. Single piece anchor abutment 401 has insertion end 402 and distal end 403, which is characterized by concave surface 404 which substantially hemispherical, and further has formed in it hollow 405.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

The invention claimed is:

1. An angularly settable dental device for anchoring a dental appliance to a patient's mouth, comprising:
    a single piece anchor abutment, having an insertion end and a distal end, said distal end having a concave surface that is a smooth hemispherical curvature and having formed therein a first hollow, and said insertion end having an exterior surface that is threaded;
    a pivotable collar having a convex bottom that is a smooth hemispherical curvature and further having formed through it a second hollow extending from top to bottom;
    wherein said pivotable collar has formed on an exterior face a circumferential indent, disposed parallel to the second hollow, and configured to receive a mating surface of an interior side wall of a top cap;
    a retention device, having an insertion end and a distal end, wherein the distal end has an outer circumference that increases in diameter along an outward curvature from the insertion end;
    said retention device configured to extend partially through said pivotable collar, wherein the distal end of the retention device is configured to engage with a side wall of the second hollow of the pivotable collar so that said insertion end of said retention device is interconnected with said first hollow; and
    wherein said pivotable collar is configured to pivotally rest against said concave surface of said abutment, whereby the orientation of said pivotable collar goes from being adjustable to being fixed when the insertion end of the retention device is interconnected with the first hollow and the distal; end of the retention device is engaged with the side wall of the second hollow of the pivotable collar.

2. The dental device of claim 1, further comprising the top cap, wherein said side wall of the top cap is joined to a top surface, and wherein an exterior of said side wall has disposed from it a horizontal circumferential ridge configured for interconnection with a denture.

3. The dental device of claim 2, wherein said first hollow is threaded and said retention device is an attachment screw.

4. The dental device of claim 2, wherein said top cap is contained within a metal enclosure.

5. The dental device of claim 3, wherein said distal end of said attachment screw has a circumference that is larger than a circumference of a threaded end of said attachment screw and said attachment screw is substantially disposed within said second hollow of said collar when said insertion end of said attachment screw is interconnected with said first hollow of said single piece anchor abutment.

6. A dental device for anchoring a dental appliance to a patient's mouth, comprising:
   an anchor, having an insertion end and a distal end, said distal end having formed therein a first hollow that is threaded, and said insertion end having an exterior that is threaded;
   an abutment, having an insertion end and a distal end, said distal end characterized by a substantially concave surface and having formed therein a second hollow that is threaded;
   said insertion end of said abutment being connectable within said first hollow;
   a pivotable collar having a substantially hemispherical convex bottom and further having formed through it a third hollow extending from top to bottom;
   wherein said pivotable collar has formed on an exterior face a circumferential indent, disposed parallel to the second hollow, and configured to receive a mating surface of an interior side wall of a top cap;
   said bottom of said pivotable collar configured to pivotally rest against said concave surface of said abutment;
   an attachment screw, having an insertion end and a distal end, wherein
      the distal end has an outer circumference that increases in diameter along an outward curvature from the insertion end; and
   said attachment screw configured to extend partially through said collar so that said insertion end of said attachment screw is interconnected with said second hollow, and the distal end of the attachment screw is engaged with a side wall of the third hollow of the pivotable collar so as to secure said collar to said abutment, whereby the orientation of said pivotable collar goes from being adjustable to being fixed when said retention screw is interconnected with said second hollow and the distal end of the attachment screw is engaged with the side wall of the third hollow.

7. The dental device of claim 6, further comprising the top cap, wherein said side wall of the top cap is joined to a top surface, and wherein an exterior of said side wall has disposed from it a horizontal circumferential ridge configured for interconnection with a denture.

8. The dental device of claim 7, wherein said convex bottom of said pivotable collar is textured effective to facilitate the fixable engagement of said pivotable collar and said abutment.

9. The dental device of claim 7, wherein said top cap is contained within a metal enclosure.

\* \* \* \* \*